(12) United States Patent
Krepinsky et al.

(10) Patent No.: US 8,133,737 B2
(45) Date of Patent: *Mar. 13, 2012

(54) SYSTEMS AND METHODS FOR BREAST CANCER DETECTION AND RISK ASSESSMENT

(75) Inventors: Jiri Jan Krepinsky, Wiarton (CA); Rudolf Furrer, Toronto (CA); Ka Sing Yeung, Wiarton (CA)

(73) Assignee: Atossa Genetics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/018,271

(22) Filed: Jan. 31, 2011

(65) Prior Publication Data

US 2011/0124110 A1 May 26, 2011

Related U.S. Application Data

(63) Continuation of application No. 11/958,597, filed on Dec. 18, 2007, now Pat. No. 7,879,614, which is a continuation of application No. 10/530,610, filed as application No. PCT/CA03/01553 on Oct. 9, 2003, now abandoned.

(60) Provisional application No. 60/417,918, filed on Oct. 11, 2002.

(51) Int. Cl.
G01N 33/48 (2006.01)
G01N 21/00 (2006.01)

(52) U.S. Cl. .......................................... 436/64; 436/164

(58) Field of Classification Search .................. None
See application file for complete search history.

(56) References Cited

U.S. PATENT DOCUMENTS

| | | |
|---|---|---|
| 65,978 A | 6/1867 | Wilder et al. |
| 3,229,691 A | 1/1966 | Crowe, Jr. |
| 3,782,377 A | 1/1974 | Rychlik |
| 3,786,801 A | 1/1974 | Sartorius |
| 3,840,012 A | 10/1974 | Rushton, Jr. |
| 3,867,517 A | 2/1975 | Ling |
| 4,036,945 A | 7/1977 | Haber |
| 4,195,639 A | 4/1980 | Lee |
| 4,302,438 A | 11/1981 | Zech |
| 4,311,688 A | 1/1982 | Burchiel et al. |
| 4,333,471 A | 6/1982 | Nakai |
| 4,376,110 A | 3/1983 | David et al. |
| 4,640,288 A | 2/1987 | Hattori |
| 4,667,666 A | 5/1987 | Fryslie |
| 4,732,864 A | 3/1988 | Tolman |
| 4,754,750 A | 7/1988 | Imonti |
| 4,870,977 A | 10/1989 | Imonti |
| 4,917,112 A | 4/1990 | Kalt |
| 5,032,103 A | 7/1991 | Larsson |
| 5,230,350 A | 7/1993 | Fentress |
| 5,348,860 A | 9/1994 | Shamsuddin |
| 5,416,025 A | 5/1995 | Krepinsky et al. |
| 5,627,034 A | 5/1997 | Gould et al. |
| 5,740,550 A | 4/1998 | Yavitz |
| 5,743,272 A | 4/1998 | Kocher, Jr. |
| 5,798,266 A | 8/1998 | Quay et al. |
| 5,910,125 A | 6/1999 | Cummings et al. |
| 6,005,159 A | 12/1999 | Spier |
| 6,036,029 A | 3/2000 | Gommel et al. |
| 6,063,029 A | 5/2000 | Saita et al. |
| 6,093,160 A | 7/2000 | Augustine et al. |
| 6,096,943 A | 8/2000 | Maiwald |
| 6,168,779 B1 | 1/2001 | Barsky et al. |
| 6,187,591 B1 | 2/2001 | Krepinsky et al. |
| 6,221,622 B1 | 4/2001 | Love et al. |
| 6,287,521 B1 | 9/2001 | Quay et al. |
| 6,570,050 B2 | 5/2003 | Augustine et al. |
| 7,487,779 B2 | 2/2009 | Kurz et al. |
| 2001/0034038 A1 | 10/2001 | Hung |
| 2001/0039015 A1 | 11/2001 | Sauter |
| 2002/0117169 A1 | 8/2002 | Kurz et al. |
| 2006/0030787 A1 | 2/2006 | Quay |
| 2006/0246415 A1 | 11/2006 | Krepinsky et al. |
| 2009/0250074 A1 | 10/2009 | Kurz et al. |

FOREIGN PATENT DOCUMENTS

| | | |
|---|---|---|
| DE | 39 07 007 | 9/1990 |
| EP | 1 377 337 | 4/2007 |
| EP | 1 554 584 | 5/2008 |
| FR | 792 353 | 12/1935 |
| GB | 2 150 028 | 6/1985 |
| WO | WO 95/14927 | 6/1995 |
| WO | WO 02/068038 | 9/2002 |
| WO | WO 2004/034059 | 4/2004 |
| WO | WO 2008/141318 | 11/2008 |

OTHER PUBLICATIONS

Bobo et al., "Findings From 752081 Clinical Breast Examinations Reported to a National Screening Program From 1995 Through 1998", Journal of the National Cancer Institute (2000); 92(12): 971-976.

Borg et al., "BRCA1 1675delA and 1135insA Account for One Third of Norwegian Familial Breast-Ovarian Cancer and Are Associated with Later Disease Onset than Less Frequent Mutations", Disease Markers (1999); 15: 79-84.

Bradwell et al., "Developments in Antibody Imaging", in Monoclonal antibodies for cancer detection and therapy (Baldwin RW, Ed.). Academic Press, New York 1985, pp. 65-85.

Breen et al., "Changes in the Use of Screening Mammography: Evidence from the 1987 and 1990 National Health Interview Surveys", American Journal of Public Health (1994); 84(1): 62-67.

(Continued)

*Primary Examiner* — Rebecca Prouty
*Assistant Examiner* — Paul Martin
(74) *Attorney, Agent, or Firm* — Wilson, Sonsini, Goodrich & Rosati

(57) ABSTRACT

The invention relates to a simple screening test for neoplasia, a precancerous condition, or cancer of the breast. A method is described whereby a breast cancer marker is detected in breast fluid. In a particular embodiment, the method involves treating samples of breast fluids with an aldehyde detecting reagent without any prewashing. The appearance in breast fluids of a marker that is detected by an aldehyde detecting reagent, such as a Schiff's reagent, correlates very well with the disease status of the breast cancer subjects from which the fluids were obtained. Screening test kits are also provided.

14 Claims, No Drawings

OTHER PUBLICATIONS

Buckley et al., "An efficient method for labelling antibodies with"In, FEBS Lett. (1984); 166(1): 202-204.

David et al., "Protein Iodination with Solid State Lactoperoxidase", Biochemistry (1974); 13(5): 1014-1021.

Ernster et al., "Incidence of and Treatment for Ductal Carcinoma in Situ of the Breast", J. Am. Med. Assoc. (1996); 275: 913-918.

Feuer et al., "How Much of the Recent Rise in Breast Cancer Incidence Can Be Explained by Increases in Mammography Utilization?", American Journal of Epidemiology (1992); 136(12): 1423-1436.

Gotzsche et al., "Is screening for breast cancer with mammography justifiable?", The Lancet (2000); 355: 129134.

Greenlee et al., "Cancer Statistics, 2001", CA: A Cancer Journal for Clinicians (2001); 51: 15-36.

Greenwood, F.C., and Hunter, W.M., The Preparation of $^{131}$I-Labeled Human Growth Hormone of High Specific Radioactivity, Journal of Biochemistry 89:114-123, 1963.

Greenwood et at, "The Preparation of $^{131}$I-Labelled Human Growth Hormone of High Specific Radioactivity", Biochem. (1969); 113: 299-305.

Hayes, D.F., "Tumor markers for breast cancer", Anals of Oncology (1993); 4: 807-819.

Hnatowich et al., "The Preparation of DTPA-Coupled Antibodies Radiolabled with Metallic Radionuclides: an Improved Method", Journal of Immunological Methods (1983); 65: 147-157.

Holmberg et al., "Breast cancer mortality in relation to self-reported use of breast self-examination. A cohort study of 450,000 women", Breast Cancer Research and Treatment (1997); 43: 137-140.

Hunter et al., "Preparation of Iodine-131 Labelled Human Growth Hormone of High Specific Activity", Nature (1962); 194: 495-496.

Kasten, Frederick H., "The Chemistry of Schiff's Reagent", Int. Revs. Cytol. (1960); 10: 1-100.

Katagiri et al., "High proportion of missense mutations of the BRCA1 and BRCA2 genes in Japanese breast cancer families", J. Hum. Genet. (1998); 43: 42-48.

Kelsey et al., "Epidemiology and Prevention of Breast Cancer", Annu. Rev. Public Health (1996); 17: 47-67.

Krepinsky et al., "From T-antigen to plasmalogen-derived aldehydes: The identification of a marker of colorectal cancer in human rectal mucous", Can. J. Chem. (2003); 81: 109-117.

Kuhl et al., "Healthy Premenopausal Breast Parenchyma in Dynamic Contrast-enhanced MR Imaging of the Breast: Normal Contrast Medium Enhancement and Cyclical-Phase Dependency", Radiology (1997); 203: 137144.

Lee et al., "Association of Abnormal Nipple Aspirate Cytology and Mammographic Pattern and Density", Cancer Epidemiology, Biomarker & Prevention (1994); 3: 33-36.

Lee et al., "The Association of Dietary Fat with Ability to Obtain Breast Fluid by Nipple Aspiration", Cancer Epidemiology, Biomarkers & Prevention (1992); 1: 277-280.

Love et al., "Breast-duct endoscopy to study stages of cancerous breast disease", The Lancet (1996); 348: 997999.

Mandel et al., "Reducing Mortality From Colcrectal Cancer by Screening for Fecal Occult Blood", New England Journal of Medicine (1993); 328(19): 1365-1371.

Marchalonis, J.J., "An Enzymic Method for the Trace Iodination of Immunoglobulins and other Proteins", Biochem. J. (1969); 113: 299-305.

Mausner et al., "Epidemiology: An Introductory Text", pp. 242-243, W.B. Saunders, St. Louis, MO. 1974.

Merchant et al., "P Magnetic resonance phospholipid profiles of neoplastic human breast tissues", Brit. J. Cancers (1991); 63: 693-698.

Morrison et al., "Use of Lactoperoxide Catalyzed Iodination in Immunochemical Studies", Immunochemisty (1971); 8: 289-297.

Najafi et al., "Coupling Anitbody with DTPA-An Alternative to the Cyclic Anhydride", Int. J. Appl. Radiat. Isot. (1984); 35(6): 554-557.

Okazaki et al., "Relationship between Cytologic Results and the Extent of Intraductal Spread in Nonpalpable Breast Cancers with Nipple Discharge", Tumor Res. (1996); 31: 89-97.

Olsen et al., "Cochrane review on screening for breast cancer with mammography", The Lancet (2001); 358: 1340-1342.

Olsen et al., "Screening for breast cancer with mammography (Review)". 2001, Cochrane Library, issue 4, Oxford: Update Software, in press.

Petrakis et al., "Birthplace and Yield of Nipple Aspirate Fluid in Chinese Women", Cancer Epidemiology, Biomarkers & Prevention (1998); 7: 835-839.

Petrakis, Nicholas L., "Nipple Aspirate Fluid in Epidemiologic Studies of Breast Disease", Epidemiologic Reviews (1993); 15(1): 188-195.

Petrakis, Nicholas L., "Studies on the Epidemiology and Natural History of Benign Breast Disease and Breast Cancer Using Nipple Aspirate Fluid", Cancer Epidemiology, Biomarkers & Prevention (1993); 2: 3-10.

Petrakis et al., "Association of Breast fluid coloration with age, ethnicity, and cigarette smoking", Breast Cancer Research and Treatment (1988); 11: 255-262.

Petrakis, Nicholas L., "Physiologic, biochemical, and cytologic aspects of nipple aspirate fluid", Breast Cancer Research and Treatment (1986); 8: 7-19.

Ranslow et al., "Screening for Colorectal Cancer", New England Journal of Medicine (1991); 325(1); 37-41.

Rhodes et al., "$^{99m}$Tc-Labeling and Acceptance Testing of Radiolabeled Antibodies and Antibody Fragments", in Burchiel SW, Rhodes BA, Friedman BE (Eds.): Tumor imaging: The radioimmunochemical detection of cancer. Masson, New York and Paris, 1982, pp. 112-123.

Ringash, Jolie, "Preventative health care, 2001 update: screening mammography among women aged 40-40 years at average risk of breast cancer", J. Can. Med. Assoc. (2001); 164: 469-476.

Robins et al., "The structure of Schiff reagent aldehyde adducts and the mechanism of the Schiff reaction as determined by nuclear magnetic resonance spectroscopy", Can. J. Chem. (1980); 58: 339-346.

Runge et al., "Paramagnetic NMR Contrast Agents Development and Evaluation", Invest. Radiol. (1984); 19: 408-415.

Santarosa et al., "Low Incidence of BRCA1 Mutations Amoung Italian Families With Breast and Ovarian Cancer", Int. J. Cancer (1998); 78: 581-586.

Sartorius, Otto, "Breast fluid cells help in early cancer detection", Am. Med. Assoc. (1973); 224: 823-827.

Sauter et al. Biologic Markers of Risk in Nipple Aspirate Fluid are Associated with Residual Cancer and Tumour Size; British Journal of Cancer, vol. 81, No. 7 (1999) pp. 1222-1227.

Sauter et al., "Nipple aspirate fluid: a promising non-invasive method to identify cellular markers of breast cancer risk", British Journal of Cancer (1997); 76(4): 494-501.

Schaefer et al., "In Vivo Nuclear Magnetic Resonance Imaging of Myocardial Perfusion Using the Paramagnetic Contrast Agent Manganese Gluconate", JACC (1989); 14(2): 472-480.

"Self-Reported Use of Mammography and Insurance Status Amoung Women Aged greater than or equal to 40 Years—United States, 1991-1992 and 1996-1997", Morbidity and Mortality Weekly Report (1998); 47: 825-830.

Shao et al., "Nipple Aspiration in Diagnosis of Breast Cancer", Seminars in Surgical Oncology (2001); 20: 175180.

Shao et al., "The role of the breast ductal system in the diagonsis of cancer (Review)", Oncology Reports (2001); 8: 153-156.

Shreve et al., "Monoclonal Antibodies Labeled with Polymeric Paramagnetic Ion Chelates", Magnetic Resonance in Medicine (1986); 3: 336-340.

Teh et al., "The Role of Ultrasound in Breast Cancer Screening. A Consensus Statement by the European Group for Breast Cancer Screening", European Journal of Cancer (1998); 34(4): 449-450.

Wagner et al, "Denaturing High-Performance Liquid Chromatography Detects Reliably BRCA1 and BRCA2 Mutations", Genomics (1999); 62: 369-376.

Wesbey et al., "Paramagnetic Pharmaceuticals for Magnetic Resonance Imaging", Physiological Chemistry and Physics and Medical NMR (1984); 16: 145-155.

Wolf et al., "Contrast Enhancement in Biomedical NMR", Physiological Chemistry and Physics and Medical NMR (1984); 16: 93-95.

Wrensch et al., "Breast Cancer Risk Associated with Abnormal Cytology in Nipple Aspirates of Breast Fluid and Prior History of Breast Biopsy", American Journal of Epidemiology (1993); 137(8): 829-833.

Wrensch et al., "Breast Cancer Incidence in Women with Abnormal Cytology in Nipple Aspirates of Breast Fluid", American Journal of Epidemiology (1992); 135(2): 130-141.

SYSTEMS AND METHODS FOR BREAST CANCER DETECTION AND RISK ASSESSMENT

PRIORITY DATA

This application is continuation of U.S. patent application Ser. No. 11/958,597, filed Dec. 18, 2007, now U.S. Pat. No. 7,879,614 which is a continuation of U.S. patent application Ser. No. 10/530,610, filed Feb. 3, 2006, now abandoned, which is a National Stage application under 35 U.S.C. §371 of PCT Application No. PCT/CA2003/01553, filed on Oct. 9, 2003 and designating the United States. PCT/CA2003/01553, which published in English on Apr. 22, 2004 as WO2004/034059, claims the priority benefit of U.S. Provisional Patent Application No. 60/417,918, filed Oct. 11, 2002. The contents of all the applications listed above, including U.S. Provisional Patent Application No. 60/417,918, PCT Application No. PCT/CA2003/01553 and U.S. patent application Ser. No. 10/530,610 and U.S. Pat. No. 7,879,614, are hereby incorporated by reference herein in their entireties.

FIELD OF THE INVENTION

This invention relates to a simple screening test for breast cancer. A method is described whereby a breast cancer marker is detected in breast fluid.

BACKGROUND OF THE INVENTION

Breast cancer is the most common noncutaneous cancer in North American women, with an estimated 192,000 newly diagnosed cases in 2001 in the United States alone. Breast cancer also appears in males although it is rare: about 1% of the incidence in women. In Connecticut, where longitudinal cancer statistics are available, breast cancer increased about 1% a year from the 1940s to 1980. Between 1982 and 1987, it increased about 4% a year, in association with the widespread use of screening by mammography (1-4).

Because of this high incidence, breast cancer is the second most common cause of cancer-related death in women in North America, with an estimate of over 40,000 cancer fatalities in 2001, i.e. approximately 25% of breast cancer cases end in death (1). Therefore, preventing the development of breast cancer, and death from it, is an extremely important task in North America and other populations where breast cancer rates are increasing rapidly. Because there are no realistic prospects of significantly improving the cure rate once the cancer has spread, many authorities believe that breast cancer can be effectively controlled only by preventive measures, as it has been documented for colorectal cancer (5).

Primary prevention of breast cancer (i.e. averting the development of the tumor by altering biological risk factors) is not yet feasible since so little is understood of the etiology of the disease. Alternatively, secondary preventive measures (i.e. detection at an asymptomatic, treatable state) would be possible should an effective screening test be available. Indeed, breast cancer has the characteristics of a suitable candidate for the development of a screening test: (1) it is a common cause of cancer-related deaths and the disease prevalence is sufficiently high to justify the expense of a screening program; (2) once the stage of invasive cancer is reached, leading to symptoms, the mortality rate is over 25%; and (3) removal of breast cancer at its earliest, asymptomatic stage can be done by limited surgical intervention, without any significant risk. Moreover, as breast cancer may become metastatic and increasingly fatal in a short time, the opportunity to detect these neoplasms at their treatable stage is limited. Therefore a screening test which would enable early diagnosis of the disease is of utmost importance.

Principles of Screening

The goal of a medical screening program is to reduce mortality by detecting a disease at a sufficiently early stage to allow curative treatment. Usually it is not designed to diagnose a disease, but to determine which asymptomatic, apparently disease-free individuals should undergo diagnostic investigations. The effectiveness of a screening test to distinguish those who warrant further evaluation from those who do not is expressed in the following epidemiological terms: sensitivity, specificity, positive predictive value, and negative predictive value. Sensitivity is defined as the proportion of diseased individuals who have a positive test (true positives/all persons with the disease); specificity is the proportion of disease-free subjects who have a negative test (true negatives/all persons without the disease; positive predictive value is the proportion of positive tests due to the disease (true positives/all positives); negative predictive value is the proportion of negative tests due to the absence of the disease (true negatives/all negatives). Almost always, sensitivity and specificity must be traded against each other. Intuitively, it appears wise to design a screening test for a fatal disease so as to optimize sensitivity, in order to detect as many individuals with the disease as possible. It has been emphasized, however, that optimizing sensitivity brings with it a risk of reducing the specificity to such an extent that unacceptably high costs, poor compliance, and "flooding" of diagnostic facilities result. Moreover, positive predictive value which is a particularly useful expression of the value of screening test is critically dependent on specificity and on how common the occurrence of a disease is in the population screened (6).

Screening Using a Schiff's Reagent

Colorectal mucus from patients with colorectal cancer turns purple on treatment with Schiff's reagent as disclosed in U.S. Pat. No. 5,416,025 to Krepinsky et al. More specifically, in U.S. Pat. No. 6,187,591 to Krepinsky et al. it is documented that the aldehydes selected from the group consisting of the following aldehydes that are insoluble in water: hexadecanal $CH_3(CH_2)_{14}CH\!=\!\!=\!O$ commonly known as palmitaldehyde, octadecanal $CH_3(CH_2)_{16}CH\!=\!\!=\!O$ commonly known as stearaldehyde, and octadec-9-enal, $CH_3(CH_2)_7CH\!=\!\!=\!CH(CH_2)_7CH\!=\!\!=\!O$, commonly known as olealdehyde, provide markers of cancer in colorectal mucus obtained by digital rectal examination in colorectal cancer patients (U.S. Pat. No. 5,416,025 to Krepinsky et al., U.S. Pat. No. 6,187,591 to Krepinsky et al, and 7).

Current Modalities of Breast Cancer Diagnosis and Screening

Breast Self Examination (BSE)

Monthly BSE is frequently advocated, but after many large scale studies have been conducted, there is no evidence for its effectiveness (8).

Clinical Breast Examination (CBE)

Clinical breast examination (by a health care practitioner) may discover breast cancers that are not detected by the patient or by other screening methods (4), but no randomized trials of CBE as a sole screening modality have been done. Based on studies that combined CBE with other modality, CBE may be effective with a sensitivity of 70% to 80%, and specificity of close to 90% (9).

Mammography

Mammography utilizes X-rays to identify differences in breast tissue density. The examination is performed by compressing the breast firmly between a plastic plate and a plate covering an x-ray cassette which contains special x-ray film.

The density of cancer tissue is higher. This difference can be observed in conventional mammography directly on the film, or in digital mammography using computer-assisted evaluation to create breast tissue images. Mammography can identify breast cancers too small to be palpated on physical examination, and can also find ductal carcinoma in situ (DCIS), a noninvasive condition (10). Since all cancers develop as a consequence of a series of mutations, it is theoretically beneficial to diagnose these noninvasive lesions. However, whether mass screening with mammography ultimately saves lives is still a subject of heated debate. Most recently, a review published by Cochrane Library concluded that there is no evidence that mammography saves lives in the long run (11-13).

Ultrasonography

The primary role of ultrasound is the evaluation of palpable or mammographically identified masses. A review of the literature and expert opinion by the European Group for Breast Cancer Screening concluded, "there is little evidence to support the use of ultrasound in population breast cancer screening at any age" (14).

Magnetic Resonance Imaging (MRI)

MRIs have been used to evaluate palpable breast masses and to discriminate between cancer and scar, but their role in breast cancer screening has not been established (15).

DNA Analysis

Screening for breast cancer by DNA analysis is based on the presence of altered genes such as BRCA1 and BRCA2 in women with increased risk for the development of the disease (16). However, the majority of breast cancer cases (approximately 90%) are sporadic (17), i.e. no hereditary links could be identified, and therefore DNA analysis could not identify them.

Breast Secretion Fluids

It is believed that neoplastic changes occur in one breast duct at the onset of the disease and may involve other ducts as the disease progresses (20). Since cancer cells may slough off and enter into the ductal fluids, cytological examinations of fluids and identification of atypical cells has been considered as a tool to detect the presence of neoplasia and cancer. In particular, many investigations utilizing nipple aspirate fluid (18, 21-24) have been conducted and correlations of abnormal cytology of breast secretion fluids (19) with breast neoplasia and cancer have been reported (25-33). However, cytological analysis is laborious and requires relatively large volumes in order to obtain sufficient numbers of exfoliated cells, rendering this approach impractical for screening purposes.

In conclusion, there is a need for a simple screening test for breast cancer which may be used solely or in conjunction with other methods (such as clinical breast examination or mammography).

SUMMARY OF THE INVENTION

Applicants have developed a novel method for detecting neoplasia, a precancerous condition, or cancer of the breast. The method detects a breast cancer marker in samples from a subject, in particular in a sample of breast fluid. In a particular embodiment, the method involves treating a sample of breast fluid with an aldehyde detecting reagent without any prewashing.

The method was found to be useful in detecting breast cancer or neoplasia, or a predisposition to breast cancer. Using the method of the invention, samples originating from the breast of subjects with breast neoplasia, precancer, or cancer of the breast showed a detectable change after addition of an aldehyde detecting reagent. No detectable change was detected for samples that originated from the breast of subjects without any of the above conditions. The appearance in breast fluids of a marker that is detected by an aldehyde detecting reagent, such as a Schiff's reagent, was found to correlate very well with the disease status of the breast cancer subjects from which the fluids were obtained.

The method of the invention has many advantages. The method is rapid, simple, inexpensive, and provides a screening test for breast cancer that does not give a high percentage of false negative or false positive results. The method facilitates early detection of the disease and it can be used for screening of large populations. Because of its high sensitivity for neoplasms the method of the invention may replace mammography or it may reduce the number of patients undergoing mammography. The early diagnosis of the disease made possible by the screening process herein described, in combination with novel medicinals such as femara, may lower significantly the number of deaths from breast cancer although primary prevention of the disease (37) is not yet possible.

Broadly stated the present invention provides a tool for screening of asymptomatic individuals for breast cancer and a screening test to detect early changes in the breast which eventually lead to breast cancer.

In an aspect of the invention, a method is provided for detecting neoplasia, a precancerous condition, or cancer of the breast in a subject comprising treating a sample of breast fluid from the subject with an aldehyde detecting reagent where the detection of a change produced by the aldehyde detecting reagent compared to a control (e.g. normal subject) is indicative of neoplasia, a precancerous condition, or cancer of the breast. The absence of a change may indicate that the subject does not have neoplasia, a precancerous condition, or cancer of the breast.

In an aspect of the invention, a method is provided comprising the following steps:

(a) obtaining a sample of breast fluid from a subject;
(b) depositing the sample on a solid support;
(c) treating the sample with an aldehyde detecting reagent without any prewashing; and
(d) detecting a colorimetric change produced in the sample, where detection of a colorimetric change compared to a control is indicative of neoplasia, a precancerous condition, or cancer of the breast.

In another aspect of the invention, a method is provided comprising the following steps:

(a) obtaining a sample of breast fluid from a subject;
(b) depositing the sample on a solid support;
(c) treating the sample with an aldehyde detecting reagent, without any prewashing, wherein the reagent reacts with aldehydes in the sample to form an adduct that adheres to the solid support; and
(d) detecting a calorimetric change produced in the sample, where detection of a colorimetric change compared to a control is indicative of neoplasia, a precancerous condition, or cancer of the breast.

In an embodiment the aldehyde detecting reagent is a Schiff's reagent and the change produced by the Schiff's reagent is a calorimetric change (i.e. purple coloration). Thus, the invention provides a method for detecting a neoplasia, a precancerous condition, or cancer of the breast in a subject, which method comprises:

a) obtaining a sample of breast fluid from a subject;
b) depositing the sample on a solid support;
c) treating the sample on the support with a Schiff's reagent without any prewashing; and d) detecting a colorimetric change resulting from the reaction of the sample and Schiff's reagent wherein a calorimetric change is indicative of neoplasia, precancer or cancer of the breast.

In an embodiment, the invention provides a method for detecting a neoplasia, a precancerous condition, or cancer of the breast in a subject, which method comprises:
 a) obtaining a sample of breast fluid from a subject;
 b) depositing the sample on a solid support;
 c) treating the sample on the support with a Schiff's reagent without any prewashing;
 d) washing the support carrying the sample;
 e) detecting a colorimetric change resulting from the reaction of the sample and Schiff's reagent wherein a calorimetric change is indicative of neoplasia, precancer or cancer of the breast.

In an embodiment, the invention provides a method for detecting a neoplasia, a precancerous condition, or cancer of the breast in a subject, which method comprises:
 a) obtaining a sample of breast fluid from a subject;
 b) depositing the sample on a solid support;
 c) treating the sample on the support with a Schiff's reagent without any prewashing;
 d) observing color formation produced in the sample;
 e) washing the support; and [0048] f) detecting a colorimetric change resulting from the reaction of the sample and Schiff's reagent wherein a colorimetric change is indicative of neoplasia, precancer or cancer of the breast.

In an embodiment of the invention a method for detecting the presence of a precancerous condition, neoplasia or cancer of the breast is provided which method consists essentially of obtaining a sample of breast fluid from a subject, treating the sample without any prewashing step with a Schiff's reagent, and detecting a precancerous condition, neoplasia or cancer of the breast based upon the coloration produced in the sample by the treatment.

In a particular embodiment, a method for detecting the presence of neoplasia, a precancerous condition, or cancer of the breast is provided, which method consists essentially of obtaining a sample of breast secretion from the breast of a subject; treating said sample with a Schiff's reagent; and, detecting neoplasia, a precancerous condition, or cancer of the breast based upon the purple coloration produced in said sample by said treatment.

The invention contemplates a method for detecting the presence of neoplasia, or cancer of the breast, which method comprises (a) obtaining a sample of breast secretion fluids which includes breast discharge, ductal secretion including single duct secretion, and nipple aspirate fluid from the nipple of one or both non-lactating breasts of a subject; (b) depositing the collected sample on a solid water-insoluble support; (c) treating the sample on the support with Schiff's reagent without any prewashing; (d) washing the sample; and (e) screening for neoplasia or cancer of the breast by persistent purple coloration produced in the sample.

Breast fluid may contain a variety of substances, one or more being aldehydes and their precursors (e.g. plasmalogens), of which one or more is a marker which by virtue of its solubility in water is susceptible to being removed in a prewash before treatment with an aldehyde detecting reagent e.g. Schiff's reagent. Some of the aldehydes upon reaction with an aldehyde detecting reagent (e.g. Schiff's reagent) may form an adduct that strongly adheres to a support and cannot be removed by washing. The aldehydes may be low molecular weight aldehydes that are soluble in water. The aldehydes may be targeted to detect breast cancer, neoplasia, or a precancerous condition. The aldehyde markers found in untreated breast fluid that react with a Schiff's reagent are referred to herein as "aldehyde marker(s) associated with breast cancer" or "aldehyde markers". The markers may be further characterized as low molecular weight aldehydes that are soluble in water. In certain aspects of the invention the term includes precursors of the aldehydes. The aldehydes may be used in the diagnostic evaluation of breast cancer or neoplasia, and the identification of subjects with a predisposition to breast cancer.

Thus, the invention provides a method for detecting neoplasia, a precancerous condition, or cancer of the breast in a subject comprising obtaining from the subject a sample suspected of containing an aldehyde marker associated with breast cancer, and detecting the presence of the aldehyde marker in the sample.

In an aspect the invention provides a method for detecting neoplasia, a precancerous condition, or cancer of the breast in a subject comprising:
 (a) obtaining a sample of breast fluid from the subject;
 (b) detecting in the sample one or more aldehyde markers associated with breast cancer, and
 (c) comparing to a control or standard.

A control or standard may correspond to results obtained for samples from healthy control subjects, from subjects with benign disease, subjects with late stage disease, or from other samples of the subject. In a preferred embodiment, the control or standard is a healthy control or disease-free subject.

Increased levels of an aldehyde marker as compared to the standard may be indicative of breast cancer. According to a method of the invention the levels of aldehyde marker associated with breast cancer in a sample from a patient is compared with the normal levels of the marker in samples of the same type obtained from controls (e.g. samples from individuals not afflicted with disease). Significantly altered levels in the sample of the marker relative to the normal levels in a control is indicative of disease. Significantly altered levels or significantly different levels of markers in a patient sample compared to a control or standard (e.g. normal levels or levels in other samples from a patient) may represent levels that are higher or lower than the standard error of the detection assay.

In an embodiment, the invention relates to a method for detecting neoplasia, a precancerous condition, or cancer of the breast in a subject by quantitating one or more aldehyde marker associated with breast cancer in a sample of breast fluid from the subject comprising (a) treating the sample with an aldehyde detecting reagent; and (b) measuring a detectable change produced by the aldehyde detecting reagent in the presence of an aldehyde marker; wherein a change in the amount or level of the detectable change compared to a control is indicative of neoplasia, a precancerous condition, or cancer of the breast.

The invention also contemplates the methods described herein using multiple markers for breast cancer. Therefore, the invention contemplates a method for analyzing a sample for the presence of one or more aldehyde markers associated with breast cancer and other markers that are indicators of breast cancer. Other markers include but are not limited to a member of the HER family of receptor tyrosine kinases, estrogen receptor, interleukins, cadherins (e.g. E-cadherin), BRCA1, and BRCA2. The methods described herein may be modified by including reagents to detect the additional markers.

The invention further relates to a method of assessing the efficacy of a therapy for breast cancer in a subject comprising comparing:
 (a) a colorimetric change produced by treating a first sample of breast fluid from the subject with a Schiff's reagent without a prewash step, wherein the sample is obtained prior to providing at least a portion of the therapy; and (b) a calorimetric change produced by treating a second sample of breast fluid from the subject with a Schiff's reagent without a prewash step, wherein the sample is obtained following therapy.

A significant difference between the calorimetric change in the second sample (e.g. colorless) relative to the first sample is an indication that the therapy is efficacious for inhibiting breast cancer.

The "therapy" may be any therapy for treating breast cancer including but not limited to therapeutics, radiation, immunotherapy, gene therapy, and surgical removal of tissue. Therefore, the method can be used to evaluate a subject before, during, and after therapy.

In an aspect, the invention provides a method for monitoring the progression of breast cancer in a subject the method comprising:

(a) detecting a colorimetric change produced by treating a sample of breast fluid from the subject obtained at a first point in time with a Schiff's reagent without a prewash step, (b) repeating step (a) at a subsequent point in time; and (c) comparing the colorimetric change detected in (a) and (b), and therefrom monitoring the progression of the breast cancer.

The invention also relates to a method for imaging a breast tumor from a subject comprising:

(a) incubating the tumor with an aldehyde detecting reagent for a sufficient period of time to permit the aldehyde detecting reagent to react with aldehyde markers associated with breast cancer, where the reagent carries a label for analyzing the tumor;

(b) detecting the presence of the label localized to the tumor.

In accordance with an aspect of the invention an in vivo method is provided comprising administering to a subject a reagent that has been constructed to target one or more aldehyde markers associated with breast cancer.

The invention therefore contemplates an in vivo method comprising administering to a mammal one or more reagent that carries a label for imaging and reacts with aldehyde markers associated with breast cancer, and then imaging the mammal.

According to a preferred aspect of the invention, an in vivo method for imaging breast cancer is provided comprising:

(a) injecting a subject with a reagent that reacts with an aldehyde marker associated with breast cancer, the reagent carrying a label for imaging the breast cancer;

(b) allowing the reagent to incubate in vivo and react with the aldehyde marker associated with breast cancer; and (c) detecting the presence of the label localized to the breast cancer.

In another embodiment of the invention the reagent is a chemical entity which recognizes the aldehyde marker.

The reagent carries a label to image the aldehyde markers. Examples of labels useful for imaging are radiolabels, fluorescent labels (e.g fluorescein and rhodamine), nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes can also be employed.

The invention also contemplates the localization or imaging methods described herein using multiple markers for breast cancer. For example, a method for imaging breast cancer may further comprise injecting the patient with one or more of an agent that binds to a member of the HER family of receptor tyrosine kinases, estrogen receptor, interleukins, cadherins (e.g. E-cadherin), BRCA1, and BRCA2.

The invention also provides kits for carrying out the methods of the invention.

These and other aspects of the present invention will become evident upon reference to the following detailed description.

DETAILED DESCRIPTION OF THE INVENTION

In accordance with the present invention there may be employed conventional biochemistry and organic chemistry techniques within the skill of the art. Such techniques are explained fully in the literature. Unless otherwise indicated, all terms used herein have the same meaning as they would to one skilled in the art of the present invention.

As hereinbefore mentioned, the present invention provides a method for screening, monitoring, diagnosing, or for the prognosis of breast cancer in a subject by treating an aldehyde detecting reagent with a sample from the subject and detecting a change produced by the reagent compared to a control. Methods are also contemplated for detecting an aldehyde marker associated with breast cancer in a sample from the subject.

The term "subject" refers to a warm-blooded animal such as a mammal which is afflicted with or suspected to be afflicted with breast cancer. Preferably, "subject" refers to a human.

The terms "detecting" or "detect" include assaying, quantitating, imaging or otherwise establishing the presence or absence of cancer or neoplasia of the breast or an aldehyde marker associated with breast cancer, or precursors thereof, and the like, or assaying for, imaging, ascertaining, establishing, or otherwise determining one or more factual characteristics of breast cancer, metastasis, stage, or similar conditions. The term encompasses diagnostic, prognostic, and monitoring applications. The methods can be used to detect the presence of cancer metastasis. They can further be used to monitor cancer chemotherapy and cancer reappearance.

The methods of the invention are carried out using a sample known or suspected of containing a marker that reacts with an aldehyde detecting reagent. Preferably the sample contains an aldehyde marker associated with breast cancer. Preferably a sample is obtained from breast fluid of a subject.

"Breast fluid" refers to a fluid produced by ducts within one or both non-lactating human breasts. The fluid inside a duct is secreted continuously and retained long enough to accumulate a variety of secreted substances and exfoliated epithelial cells (27-33). The fluids include but are not limited to breast nipple discharge, breast nipple aspirates, fluids obtained by pressure, and fluids collected by endoscopic methods. "Breast discharge" means fluid produced by ducts within the breast which appears spontaneously on the surface of the nipple; it may contain blood (18). A breast discharge may be a single duct secretion. "Breast aspirates" mean fluids produced by ducts within the breast which are brought to the surface of the nipple by gentle suction using a variety of simple suction devices. "Fluids obtained by pressure" means fluids produced by ducts within the breast and brought to the surface of the nipple by applying pressure on the breast, in particular with human hands. "Fluids collected by endoscopic methods" means fluids produced by ducts within the breast and collected by inserting an endoscopic device into the ducts (19).

A breast fluid can be obtained by conventional methods known to the skilled artisan. Endoscopic collection of fluid from individual breast ducts is carried out by standard methods (see U.S. Pat. No. 6,221,622 to Love et al.; U.S. Pat. No. 6,168,779 to Barsky et al. U.S. Pat. Nos. 6,287,521 and 5,798,266 to Quay et al.). The collection of breast fluid at the ductal orifice on the nipple surface is a much simpler method of obtaining such a fluid. It is obtainable from some women when they squeeze their breast with both hands—droplets of the fluid appear at the duct orifice on the nipple. More commonly, the fluid can be aspirated from the breast of non-lactating women through the duct opening in the nipple using a simple non-invasive pump (see U.S. Pat. No. 3,786,801 to Sartorius). Droplets that appear at the duct orifice on the nipple or the duct opening are collected into a capillary tube or directly deposited on a solid support e.g. a fabric support.

A breast fluid from a screened subject is preferably deposited on a suitable water-insoluble substrate or support, such as a pad or disc, either before or after reaction with an aldehyde detecting reagent. A support material may be prepared from, for example, glass microfibres, some polymer fibres such as polyester fibres (e.g. polymacron [Dupont]), and cellulose or modified cellulose fibers. Suitable support materials are, for example, glass microfibres WHATMAN™ GF/C, polymer fibres such as Biotrace RP, METRICEL™ DM 450, METRICEL™ VM-1, SEPRAPHORE™ III, VERSAPORE™ 450, or cellulose fibre such as WHATMAN™ 3 MM. The support may or may not be pre-treated with an antioxidant such as BHT (butylated hydroxytoluene) or BHA (butylated hydroxyanisol). A support may be in the shape of, for example, a tube, test plate, well, beads, disc, sphere etc.

A sample screened in a method of the invention, (e.g. a breast fluid sample) should not be pretreated or modified so as to remove or damage aldehyde markers associated with breast cancer in the sample. In particular, a sample screened in a method of the invention should not be treated or washed with aqueous solutions such as water or buffers prior to treatment with an aldehyde detecting reagent. Aldehyde markers in a sample may be soluble in water and may be removed if the sample is washed prior to treatment with the reagent.

A method of the invention utilizes an aldehyde detecting reagent. An "aldehyde detecting reagent" refers to a reagent that is capable of detecting an aldehyde, in particular an aldehyde marker associated with breast cancer in a mixture. Typically the reagent specifically reacts with aldehyde groups or aldehydic group forming compounds and it is detectable by suitable properties such as color, (i.e. a colorimetric change, for example, specific spectral properties, fluorescence, chemiluminescence, and other biological reactions detectable by color), mass spectral properties, and chromatographic properties. Many aldehyde detecting reagents may be used in the practice of the invention. Suitable aldehyde detecting reagents include compounds containing amino groups that under acidic conditions form addition compounds with aldehydes and have detectable properties such as color or fluorescence. In a preferred embodiment of the invention, the aldehyde detecting reagent is a Schiff's reagent. A Schiff's reagent employed in methods of the invention reacts with aldehydes with high sensitivity to form a purple or purple-magenta color addition compound (34, 35).

A Schiff's reagent may be prepared in accordance with standard methods or obtained from commercial sources. A particularly sensitive and specific method results from using the Schiff's reagent prepared as illustrated herein (e.g. see Example 1). In some circumstances it is desirable to allow the reagent to mature for between 4 days to 6 weeks at 3° C. to 5° C. before use. In a particular embodiment, the reagent is allowed to mature for about 4 days at room temperature.

A sample is generally treated with an aldehyde detecting reagent under conditions suitable for the reagent to produce a detectable change in the presence of an aldehyde, in particular an aldehyde marker associated with breast cancer. Typically the sample is reacted with an aldehyde detecting reagent at about 15-30° C., in particular 20-25° C. An aldehyde detecting reagent may be sprayed on a sample deposited on a solid support, the solid support with the deposited sample may be inserted into an aldehyde detecting reagent, or the sample may be applied to a solid support comprising an aldehyde detecting reagent. A detectable change may be formed between about 2 to 60 minutes, in particular 10 to 20 minutes, more particularly about 20 minutes. The sample is washed with an aqueous solution, preferably water, for a sufficient period of time to remove surplus aldehyde detecting reagent. A positive reaction is scored when a permanent detectable change is detected. When the aldehyde detecting reagent is a Schiff's reagent, a positive reaction is scored when a purple or purple-magenta color is formed. However, different shades of color may be observed that may correlate with the clinical condition of a subject e.g. late stage disease. The color change may also be detected by absorption spectroscopy, for instance using a reflectance probe. When a marker is absent, the support remains colorless although some background coloration may be present.

A general procedure for use in the implementation of the invention is as follows.

A nipple aspirate fluid sample obtained by a physician, a trained nurse, or a subject from a breast is deposited on a suitable water-insoluble substrate or support, such as a pad or a disc. The support with the deposited nipple aspirate fluid sample is sprayed with Schiff's reagent from an atomizer and the specimen becomes strongly red colored. Twenty minutes after exposure to Schiff's reagent, the plates are repeatedly washed with distilled water, while gently agitated, for a period of about 10 minutes, with a change of water about every three minutes until the washing water is no longer colored. Usually three washings with water are sufficient. Alternatively, a specimen deposited on a support is briefly inserted into Schiff's reagent, preferably for no more than about 1 minute; the specimen becomes red colored and after about 20 minutes it is washed repeatedly with water while gently agitated until the water is no longer colored as described hereinabove. A positive reaction is scored when permanent purple color remains on the support.

If a specimen does not produce any coloration, it may be because of the absence of the markers or their precursors from the nipple aspirate fluid, or because insufficient quantity of the fluid was deposited on the support. When an aspirate fluid lacking the marker is involved, red coloration appears at the place where the fluid was deposited shortly after treatment with Schiff's reagent, but the color is completely removed when the colored specimen is subjected to repeated washings. If insufficient amount of the aspirate fluid was deposited, weak initial red coloration appears after treatment with Schiff's reagent, but the color is removed by washing (as above).

During the practice of a particular process according to the invention, the initial color formed is due to the red dye p-rosaniline reflecting the decomposition of Schiff's reagent from which the dye is liberated. This color is soluble in water and it is removed by washing with water. As described hereinabove, the purple color of the marker cannot be removed by washing with water.

The properties of a Schiff's reagent may vary according to the combination of various isomers present in commercial preparations of p-rosaniline and according to the method of preparation of the Schiff's reagent itself. The preferable procedure for the preparation of an appropriate Schiff's reagent is described herein. To obtain reproducible results with maximum sensitivity and stability, it is recommended to allow the reagent to mature at room temperature for about four days before use.

The support (substrate) may generally be exposed through a circular aperture (1.0-1.3 cm diameter) between two tightly sealed rectangular hard plastic plates. The dimensions of the sealed assembled plates may be those of microscope slides which would make it possible to utilize the equipment standard for the simultaneous treatment of microscope slides.

In a particular embodiment of the invention, the support comprises a frame assembly. The frame assembly comprises a pair of rectangularly shaped plates (25 mm×75 mm×1 mm) from a hard plastic resistant to acids, resembling the plastic used to manufacture credit cards. A circular aperture (1.0-1.3 cm in diameter) appears centered at about 12.5 mm from three sides of the plate. The support fabric, comprising fabric from glass or polyester fibre, giving no color reaction with Schiff's reagent, is placed in between the two superimposed plates sealed together thermally or using a glue or adhesive tapes. The support is accessible on both sides to deposit the nipple fluid obtained from a subject; the fluid is deposited on one side only.

In operation, a physician or nurse places a specimen of the nipple fluid onto the surface of the support in the plate's aperture. The plates are transferred to a laboratory to be processed individually or in batches the size of which is determined by the equipment utilized in the practice of the test. The plates are discarded after the results are read. If color is difficult to be certain of, the plates may be read at a later point in time, in particular one to seven days later.

A process is hereinbelow described as a screening test for the early detection of neoplasia, precancer, or cancer of the breast Onto the support secured in the plate as described hereinabove and convenient to handle is deposited a specimen of the nipple fluid. The plates with the deposited specimens are temporarily stored at −20° C. and transferred to a processing laboratory in a container cooled by dry ice. Upon arrival the plates are removed from the dry-ice container in which they were transported and stored if so required in a freezer for a prolonged period of time, such as six months, at −70° C.

To develop, the plates are removed from the freezer in which they had been stored, allowed to warm up to room temperature (21° C.), and kept at that temperature for at least 4-5 hours so that they can sufficiently adhere to the support before starting the treatment with Schiff's reagent.

More specifically, for processing, the following method has been found suitable. Individual plates with deposited nipple fluid allowed to warm up to room temperature are sprayed with Schiff's reagent described hereinbelow and allowed to develop red color within 20 minutes. Then the plates are washed by immersing the plates into a glass container with distilled water for approximately three minutes, and the washing is repeated three times for the total washing time of approximately 10 minutes. The last washing water usually becomes colorless. Approximately 30 minutes after exposure to Schiff's reagent, including washing time, the plates are scored by reading the remaining purple color.

It should be noted that a weakly positive test result is to be expected if only a small amount of the fluid is present on the support, and thus it has the same validity as a strongly positive result of an abundant fluid sample.

The methods described herein may be modified by including reagents to detect additional markers associated with breast cancer. Other markers include but are not limited to a member of the HER family of receptor tyrosine kinases, estrogen receptor, interleukins, cadherins (e.g. E-cadherin), BRCA1, and BRCA2.

The invention provides a method for imaging tumors associated with an aldehyde marker associated with breast cancer. The invention also contemplates imaging methods described herein using multiple markers for breast cancer. For example, a method for imaging breast cancer may utilize a reagent that reacts with one or more aldehyde marker associated with breast cancer and one or more of a reagent that binds to a member of the HER family of receptor tyrosine kinases, estrogen receptor, interleukins, cadherins (e.g. E-cadherin), BRCA1, and BRCA2. In a particular embodiment, each reagent is labeled so that it can be distinguished during the imaging.

In an embodiment the method is an in vivo method and a subject or patient is administered one or more reagents that carry an imaging label and that are capable of targeting or treating with an aldehyde marker associated with breast cancer. The reagent is allowed to incubate in vivo and reacted with an aldehyde marker associated with breast cancer. The presence of the label is localized to the breast cancer, and the localized label is detected using imaging devices known to those skilled in the art.

The reagent may be an antibody or chemical entity which reacts with the aldehyde marker. The reagent carries a label to image the aldehydes. The reagent may be labelled for use in radionuclide imaging. In particular, the reagent may be directly or indirectly labelled with a radioisotope. Examples of radioisotopes that may be used in the present invention are the following: $^{277}$Ac, $^{211}$At, $^{128}$Ba, $^{131}$Ba, $^{7}$Be, $^{204}$Bi, $^{205}$Bi, $^{206}$Bi, $^{76}$Br, $^{77}$Br, $^{82}$Br, $^{109}$Cd, $^{47}$Ca, $^{11}$C, $^{14}$C, $^{36}$Cl, $^{48}$Cr, $^{51}$Cr, $^{62}$Cu, $^{64}$Cu, $^{67}$Cu, $^{65}$Dy, $^{155}$Eu, $^{18}$F, $^{153}$Gd, $^{66}$Ga, $^{67}$Ga, $^{68}$Ga, $^{72}$Ga, $^{198}$Au, $^{3}$H, $^{166}$Ho, $^{111}$In, $^{113m}$In, $^{115m}$In, $^{123}$I, $^{125}$I, $^{131}$I, $^{189}$Ir, $^{191m}$Ir, $^{192}$Ir, $^{194}$Ir, $^{52}$Fe, $^{55}$Fe, $^{59}$Fe, $^{177}$Lu, $^{15}$O, $^{191m-191}$Os, $^{109}$Pd, $^{32}$P, $^{33}$P, $^{42}$K, $^{226}$Ra, $^{186}$Re, $^{188}$Re, $^{82m}$Rb, $^{153}$Sm, $^{46}$Sc, $^{47}$Sc, $^{72}$Se, $^{75}$Se, $^{105}$Ag, $^{22}$Na, $^{24}$Na, $_{89}$Sr, $^{35}$S, $^{38}$S, $^{177}$Ta, $^{96}$Tc, $^{99m}$Tc, $^{201}$Tl, $^{202}$Tl, $^{113}$Sn, $^{117m}$Sn, $^{121}$Sn, $^{166}$Yb, $^{169}$Yb, $^{175}$Yb, $^{88}$Y, $^{90}$Y, $^{62}$Zn and $^{65}$Zn. Preferably the radioisotope is $^{131}$I, $^{125}$I, $^{123}$I, $^{111}$I, $^{99m}$Tc, $^{90}$Y, $^{186}$Re, $^{188}$Re, $^{32}$P, $^{153}$Sm, $^{67}$Ga, $^{201}$Tl $^{77}$Br, or $^{18}$F, and is imaged with a photoscanning device.

Procedures for labeling biological agents with the radioactive isotopes are generally known in the art. U.S. Pat. No. 4,302,438 to Zech describes tritium labeling procedures. Procedures for iodinating biological agents, such as antibodies, binding portions thereof, probes, or ligands, are described in the scientific literature (38, 39), and U.S. Pat. No. 3,867,517 to Ling and U.S. Pat. No. 4,376,110 to David et al. Iodinating procedures for agents are described in the scientific literature (40-42) as well. $^{99m}$Tc-labeling procedures are described by Rhodes, B. et al. (43). Procedures suitable for $^{111}$In-labeling biological agents are described by Hnatowich, D. J. et al. (44, 45) and Buckley, R. G. et al. (46).

A reagent may also be labeled with a paramagnetic isotope for purposes of an in vivo method of the invention. Examples of elements that are useful in magnetic resonance imaging include gadolinium, terbium, tin, iron, or isotopes thereof (See, for example, references 47 to 51, for discussions on in vivo nuclear magnetic resonance imaging.)

In the case of a radiolabeled reagent, the reagent may be administered to the subject, it is localized to the tumor having an aldehyde marker associated with breast cancer with which the agent binds, and is detected or "imaged" In vivo using known techniques such as radionuclear scanning using e.g., a gamma camera or emission tomography (e.g., 52). A positron emission transaxial tomography scanner, such as the scanner designated Pet VI located at Brookhaven National Laboratory, can also be used where the radiolabel emits positrons (e.g., $^{11}C$, $^{18}F$, $^{15}O$ and $^{13}N$).

Whole body imaging techniques using radioisotope labeled agents can be used for locating both primary tumors and tumors which have metastasized. Antibodies specific for an aldehyde marker, or fragments thereof having the same epitope specificity, are bound to a suitable radioisotope, or a combination thereof, and administered parenterally. The biodistribution of the label can be monitored by scintigraphy, and accumulations of the label are related to the presence of breast cancer cells. Whole body imaging techniques are described in U.S. Pat. No. 4,036,945 to Haber and U.S. Pat. No. 4,311,688 to Burchiel et al. Other examples of reagents useful for diagnosis and therapeutic use include metallothionein and fragments (see, U.S. Pat. No. 4,732,864 to Tolman). These agents are useful in diagnosis staging and visualization of cancer so that surgical and/or radiation treatment protocols can be used more efficiently.

The methods of the invention can be carried out using a kit. A kit may comprise, for example, a container such as a package, carton, tube, box, roll, tape, or other capsule-like object comprising a solid support and the necessary reagents to carry out a method of the invention. A kit may contain means for detecting the reaction of an aldehyde detecting reagent and an aldehyde associated with breast cancer in a sample. A support may be pre-treated with a solution of an aldehyde detecting reagent (e.g Schiff's reagent) to retain an active portion thereof; or the container may have each of the support and the reagent separately packaged; or the reagent may be generated before use from basic fuchsin deposited on the support. Where the kit is intended for in vivo use, single dosages may be provided in sterilized containers, having the desired amount and concentration of reagents.

In an embodiment of the invention, a screening kit is provided as hereinabove defined but incorporating packaged basic fuchsin instead of Schiff's reagent. The basic fuchsin is provided as a source of Schiff's reagent by subsequent reaction of sulphur dioxide or sulfite with the basic fuchsin in acidic conditions. Instead of the above, sulfur-dioxide in situ generating agents, could be used.

A screening test kit provides means for conducting a method of the invention for detecting neoplasia, a precancerous condition, or cancer of the breast in a hospital, medical laboratory or clinic, or outside a hospital or clinic.

The invention will now be illustrated by the following non-limiting examples.

EXAMPLES

Example 1

Preparation of Schiff's reagent: p-Rosaniline (0.2 g) is dissolved in hot water (100 mL); after cooling to room temperature sodium bisulfite (1.17 g) and 1N hydrochloric acid (17 mL) are added sequentially, and the solution is allowed to stand in the dark at room temperature for 4 days. Then charcoal (0.15 g) is added, mixed well, and filtered off. The resulting colourless solution is stable for a prolonged period of time in a refrigerator at +2 to +5° C.

Example 2

Sample nipple fluid was deposited on the fabric portion of the plates and stored at −70° C. in a freezer. Before processing, individual plates with deposited nipple fluid were allowed to warm up to the room temperature and kept at that temperature for 5 hours. Then the fabric portions of the plates were sprayed with Schiff's reagent described in Example 1, and allowed to develop red/purple color for 20 minutes. The plates were then placed in a glass vessel such as a "Wheaton staining dish" which was filled with distilled water and gently agitated for 3 minutes. For agitation, an orbital shaker at 65-100 RPM was used. The colored washing water was replaced by fresh distilled water, the staining dish with the plates carrying the specimens was again gently agitated for 3 minutes, and the colored water discarded. The washing was repeated three times for the total washing time of 10 minutes, with a change of water approximately every three minutes. Usually the last washing water remained colorless through washing. Then, 30 minutes after exposure to Schiff's reagent, including washing time, the plates were scored by reading the remaining purple color.

Example 3

Nipple aspirate fluid (34 specimens) from 28 subjects (12 diagnosed with cancer) age between 30 and 52 years (median 41 years) attending the Breast Care Clinic at the University of California at San Francisco had been collected using an aspirator (25, 26) well known to those experienced in the art, and four nipple fluid specimens from healthy volunteers at the University of Toronto were collected using the pressure method. The test results were positive in all subjects diagnosed with breast cancer (malignant or invasive, ductal carcinoma in situ, and lobular carcinoma in situ). The test was negative in most disease-free subjects. Exceptions were: two specimens from the high risk group (first degree relative such as mother, sister; daughter diagnosed with breast cancer) were both positive. Two individuals attending the Breast Care Clinic for unspecified reasons tested positive although they neither became diagnosed with breast cancer nor had a first degree relative with breast cancer.

REFERENCE LIST

The present specification refers to the following publications and patents, each of which is expressly incorporated herein by reference.

Publications

1. Greenlee R T, Hill-Harmon M B, Murray T, et al.: Cancer statistics, 2001. CA: A Cancer Journal for Clinicians 51, 15-36.
2. Feuer E J, Wun L M: How much of the recent rise in breast cancer incidence can be explained by increases in mammography utilization? 1992. Am. J. Epidemiol. 136, 1423-1436.
3. Self-reported use of mammography and insurance status among women aged > or =40 years—United States, 1991-1992 and 1996-1997. 1998. Morbidity and Mortality Weekly Report 47, 825-830.
4. Breen N, Kessler L: Changes in the use of screening mammography: evidence from the 1987 and 1990 National Health Interview Surveys. 1994, Am. J. Public Health 84, 62-67.
5. a) Ransohoff D F, Lang C A: Screening for colorectal cancer. 1991, New Engl. J. Med. 325, 37. b) Mandel J S, Bond J H, Church T R, Snover D C, Bradley G M, Schuman L M, Ederer F: Reducing mortality from colorectal cancer by screening for fecal occult blood. 1993, New Engl. J. Med. 328, 1365.

6. a) Mausner J S and Bahn A K: Epidemiology, An Introductory Text, pp. 242-243. W.B. Saunders, St. Louis, Mo. 1974. b) Ringash J: Canadian task Force on Preventive Health Care. Preventive health care, 2001 update. 2001, J. Can. Med. Assoc. 164, 469-76.
7. Krepinsky J J, Kandel G P, Young K S, Chociej J, Chen M, Cohen G, Douglas S P, Furrer R, Kulreti V, Lupescu N, Richens E and Tanner K L: From T-antigen to plasmalogen-derived aldehydes: The identification of a marker of colorectal cancer in human rectal mucous. 2003, Can. J. Chem. 81, 109-117.
8. Holmberg L, Ekhom A, Calle E. et al.: Breast cancer mortality in relation of self-reported use of breast self-examination. A cohort study of 450,000 women. 1997, Breast Cancer Research and Treatment 43, 137-40.
9. Bobo J K, Lee N C, Thames S F: Findings from 752,081 clinical breast examinations reported to a national screening program from 1995 through 1998. 2000, J. Natl. Cancer Inst. 92, 971-976.
10. Ernster V L, Barclay J, Kerlikowske K, et al.: Incidence of and treatment for ductal carcinoma in situ of the breast. 1996, J. Am. Med. Assoc. 275, 913-918.
11. Gotzsche P C and Olsen: Is screening for breast cancer with mammography justifiable? 2000, The Lancet 355, 129-134.
12. Olsen O and Gotzsche P C: Cochrane review on screening for breast cancer with mammography. 2001, The Lancet 358, 1340-1342.
13. Olsen O and Gotzsche P C: Screening for breast cancer with mammography. 2001, Cochrane Library, issue 4, Oxford: Update Software, in press.
14. Teh W, Wilson A R: The role of ultrasound in breast cancer screening. A consensus statement by the European Group for Breast Cancer Screening. 1998, Eur. J. Cancer 34, 449-450.
15. Kuhl C K, Bieling H B, Gieseke J, et al.: Healthy premenopausal breast parenchyma in dynamic contrast-enhanced MR imaging of the breast: normal contrast medium enhancement and cyclical-phase dependency. 1997, Radiology 203, 137-144.
16. a) Katagiri T, Kasumi F, Yoshimoto M et al.: High proportion of missense mutations of the BRCA1 and BRCA2 genes in Japanese breast cancer families. 1998, J. Hum. Genet. 43, 42-48; b) Borg A, Dorum A, Heimdal K, Maehle L, Hovig E, Moller P: BRCA1 1675delA and 1135insA account for one third of Norwegian familial breast-ovarian cancer. 1999, Dis. Markers 15, 79-84. c) Wagner T, Stoppa-Lyonnet D, Fleischmann E, Muhr D, et al.: Denaturing HPLC detects reliably BRCA1 and BRCA2 mutations. 1999, Genomics. 62, 369-376.
17. Santarosa M, Viel A, Dolcetti R, Crivellari D, et al.: Low incidence of BRCA1 mutations among Italian families with breast-ovarian cancer. 1998, Int. J. Cancer 78, 581-586.
18. Okazaki A et al.: Relationship between cytologic results and the extent of intraductal spread in non-palpable breast cancers with nipple discharge 1996, Tumor Res. 31, 89-97.
19. Love S M, Barsky S H: Breast-duct endoscopy to study stages of cancerous breast disease. 1996, The Lancet 348, 997-999.
20. Shao Z M, Liu Y H, Nguyen M: The role of the breast ductal system in the diagnosis of cancer. 2001, Oncology Reports. 8, 153-156.
21. Petralis N L: Physiologic, biochemical, and cytologic aspects of nipple aspirate fluid. 1986, Breast Cancer Research and Treatment 8, 7-19.
22. Lee M M, Wrensch M R, Miike R, Petralis N L: The association of dietary fat with ability to obtain breast fluid by nipple aspiration. 1992, Cancer Epidemiol., Biomarkers and Prevention 1, 277-280.
23. Petrakis N L, Miike R, King E B, Lee L, Mason L, Lee B C: 1988, Association of breast fluid coloration with age, ethnicity, and cigarette smoking. Breast Cancer Research and Treatment 328, 255-262.
24. Petralis N L, Lee M M, Wrensch M R, Ernster V L, Miike R, Koo L C, Ho J C: Birthplace and yield of nipple aspirate fluid in Chinese women. 1998, Cancer Epidemiol., Biomarkers and Prevention. 7, 835-839.
25. Petralis N L: Nipple aspirate fluid in epidemiologic studies of breast disease. 1993, Epidemiol. Revs. 15, 188-195.
26. Petralis N L: Studies on the epidemiology and natural history of benign breast disease and breast cancer using nipple aspirate fluid. 1993, Cancer Epidemiol., Biomarkers, and Prevention 2, 3-10.
27. Shao Z M and Nguyen M: Nipple aspiration in diagnosis of breast cancer. 2001, Seminars in Surgical Oncology. 20, 175-180.
28. Wrensch M R, Petrakis N L, King E B, Miike R, Mason L, Chew K L, Lee M M, Emster V L, Hilton J F, Schweitzer R, Goodson W H, Hunt T K: Breast cancer incidence in women with abnormal cytology in nipple aspirates of breast fluid. 1992, Amer. J. Epidemiol. 135, 130-141.
29. Sauter E.: Nipple aspirate fluid: a promising non-invasive method to identify cellular markers of breast cancer. 1997, Brit. J. Cancer 78, 494.
30. Lee M M, Petrakis N L, Wrensch M R, King E B, Miike, R, Sickles E: Association of abnormal nipple aspirate cytology and mammographic pattern and density. 1994, Cancer Epidemiol., Biomarkers and Prevention. 3, 33-36.
31. Wrensch M R, Petrakis N L, King E B, Lee M M, Miike R: Breast cancer risk associated with abnormal cytology in nipple aspirates of breast fluid and prior history of breast biopsy. 1993, Amer. J. Epidemiol. 137, 829-833.
32. Sartorius O W: Breast fluid cells help in early cancer detection. 1973, J. Am. Med. Assoc. 224, 823-827.
33. Hayes D F: Tumor markers for breast cancer. 1993, Annals Oncol. 4, 807-819.
34. Kasten F H: The chemistry of Schiff's reagent. 1960, Int. Revs. Cytol. 10, 1.
35. Robins J H, Abrams, G D, Pincock J A: The structure of Schiff's reagent aldehyde adduct and the mechanism of the Schiff's reaction as determined by nuclear magnetic resonance spectroscopy. 1980, Can. J. Chem. 58, 339.
36. Merchant T E, Meneses P, Gierke L W, Den Otter W, Glonek T: $^{31}$P Magnetic resonance phospholipid profiles of neoplastic human breast tissues. 1991, Brit J. Cancer 63, 693-698.
37. Kelsey M I: Epidemiology and prevention of breast cancer. 1996, Ann. Rev. Public Health 17, 47-6 7.
38. Hunter W M and Grenwood F C: Preparation of Iodine-131 labeled human growth hormone of high specific activity. 1962, Nature 194, 495-6.
39. David G S and Reisfeld R A: Protein iodination with solid state lactoperoxidase. 1974, Biochemistry 13, 1014-1021.
40. Greenwood F C and Hunter W M: The preparation of $^{131}$I-labeled human growth hormone of high specific radioactivity. 1963, Biochem. J. 89, 114-123.
41. Marchalonis J: An enzymic method for the trace iodination of immunoglobulins and other proteins. 1969, Biochem. J. 113, 299-305.
42. Morrison M, Sisco-Bayse G, Webster R G: Use of lactoperoxidase-catalyzed iodination in immunochemical studies. 1971, Immunochemistry 8, 289-297.

43. Rhodes B A, Torvestad D A, Breslow K, Burchiel S W, Reed K A, Austin R K: $^{99m}$Tc-labeling and acceptance testing of radiolabeled antibodies and antibody fragments in Burchiel S W, Rhodes B A, Friedman B E (Eds.): Tumor imaging: The radioimmunochemical detection of cancer. Masson, New York and Paris, 1982, pp. 112-123.
44. Hnatowich D J, Childs R L, Lanteigne D, Najafi A: The preparation of DTPA-coupled antibodies radiolabeled with metallic radionuclides: An improved method. 1983, J. Immunol. Methods 65, 147-157.
45. Najafi A, Childs R L, Hnatowich D J: Coupling antibody with DTPA—an alternative to the cyclic anhydride. 1984, Int. J. Appl. Radiation. 35, 554-557.
46. Buckley R G and Searle F: An efficient method for labeling antibodies with $^{111}$In. 1984, FEBS Lett. 166, 202-204.
47. Schaefer S, Lange R A, Kulkarni P V, Katz J, Parkey R W, Willerson J T, Peshok R M: In vitro nuclear magnetic resonance imaging of myocardial perfusion using the paramagnetic contrast agent manganese gluconate. 1989, J. Amer. College Cardiol. 14, 472-480.
48. Shreve P and Aisen A M: Monoclonal antibodies labeled with polymeric ion chelates. 1986, Magn. Reson. Medicine, 3, 336-340.
49. Wolf G L: Contrast enhancement in biomedical NMR. 1984, Physiol. Chemistry Physics Medical NMR 16, 93-95.
50. Wesbey G E, Engelstad B L, Brasch R C: Paramagnetic pharmaceuticals for magnetic resonance imaging. 1984, Physiol. Chemistry Physics Medical NMR 16, 145-155.
51. Runge V M, Clanton J A, Foster M A, Partain C L, James A B, Jr.: Paramagnetic NMR contrast agents development and evaluation. 1984, Investig. Radiol. 19, 408-415.
52. Bradwell A R, Fairweather D S, Dykes P W: Developments in antibody imaging, in Monoclonal antibodies for cancer detection and therapy (Baldwin R W, Ed.). Academic Press, New York 1985, pp. 65-85.

Patents

1. U.S. Pat. No. 5,416,025, Krepinsky et al. May 16, 1995.
2. U.S. Pat. No. 6,187,591, Krepinsky et al. Feb. 13, 2001.
3. U.S. Pat. No. 6,613,189, Haddad et al. Nov. 13, 2001.
4. U.S. Pat. No. 6,221,622, Love et al. Apr. 24, 2001.
5. U.S. Pat. No. 6,168,779, Barsky et al. Jan. 2, 2001.
6. U.S. Pat. No. 6,287,521, Quay et al. Sep. 11, 2001.
7. U.S. Pat. No. 5,798,266, Quay et al. Aug. 25, 1998.
8. U.S. Pat. No. 5,627,034, Gould et al. May 6, 1997.
9. U.S. Pat Appl. No. 20010039015, Sauter, Nov. 8, 2001.
10. U.S. Pat. Appl. No. 20010034038, Huang, Oct. 25, 2001.
11. U.S. Pat. No. 3,786,801, Sartorius, January, 1974.
12. U.S. Pat. No. 4,302,438, Zech, Jan. 8, 1980.
13. U.S. Pat. No. 3,867,517, Ling, Feb. 18, 1975.
14. U.S. Pat. No. 4,376,110, David et al, Mar. 8, 1983.
15. U.S. Pat. No. 4,036,945; Haber, Jul. 19, 1977.
16. U.S. Pat. No. 4,311,688, Burchiel et al., Jan. 19, 1982.
17. U.S. Pat. No. 4,732,864, Tolman, Mar. 22, 1988.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the cell lines, vectors, methodologies etc. which are reported therein which might be used in connection with the invention. Nothing herein is to be construed as an admission that the invention is not entitled to antedate such disclosure by virtue of prior invention.

It must be noted that as used herein and in the appended claims, the singular forms "a", "an", and "the" include plural reference unless the context clearly dictates otherwise. Thus, for example, reference to "the aldehyde marker" includes a plurality of such aldehyde markers, and so forth.

What is claimed is:

1. A method of screening a patient for breast cancer or for elevated breast cancer risk, comprising:
providing a solid support configured to receive a volume of breast aspirate fluid from the patient;
wherein the volume of breast aspirate fluid is obtained from a breast duct of a patient;
wherein the volume of breast aspirate fluid is obtained at least in part by the application of suction within or along the breast of the patient;
wherein the solid support comprises an aldehyde detecting agent; and
detecting a change in a detectable property produced by contacting the volume of breast aspirate fluid to the aldehyde detecting reagent on the solid support;
wherein the detection of a change in a detectable property produced by treating the breast fluid with the aldehyde detecting reagent compared to a control is indicative of a patient having breast cancer or elevated breast cancer risk; and
wherein the volume of breast aspirate fluid does not undergo pretreatment or modification before being placed on the solid support.

2. The method of claim 1, wherein the solid support comprises a pad.

3. The method of claim 1, wherein the detectable property comprises at least one of: color, spectral properties, spectral absorption, fluorescence, chemi-luminescence, mass spectral properties or chromatographic properties.

4. The method of claim 1, wherein the aldehyde detecting reagent comprises Schiff's reagent.

5. The method of claim 1, wherein the volume of breast aspirate fluid is additionally screened for the presence of at least one additional marker of breast cancer.

6. The method of claim 5, wherein the solid support comprises at least one additional reagent for detection of the at least one additional marker.

7. The method of claim 1, wherein the solid support comprises a water-insoluble substrate.

8. The method of claim 1, wherein a shape of the solid support is generally a tube, test plate, well, beads, disc or sphere.

9. A method for monitoring the effectiveness of a chemotherapy treatment of a patient with breast cancer, comprising:
treating a sample of breast fluid secreted from a nipple of a patient undergoing chemotherapy with an aldehyde-detecting reagent;
detecting a change in a detectable property produced by treating the sample of breast fluid with the aldehyde-detecting reagent;

wherein the detectable property comprises one or more of: color, spectral properties, spectral absorption, fluorescence, chemi-luminescence, mass spectral properties or chromatographic properties;

wherein the sample of breast fluid is treated directly with the aldehyde-detecting reagent, such that the breast fluid does not undergo pretreatment or modification prior to contacting the aldehyde-detecting reagent;

and wherein a significant reduction in the detectable property compared to a control is indicative that a chemotherapy treatment is generally effective.

10. The method of claim 9, wherein the aldehyde-detecting reagent is positioned on a solid support.

11. The method of claim 10, wherein the solid support comprises a pad.

12. The method of claim 9, wherein the aldehyde detecting reagent comprises Schiff's reagent.

13. The method of claim 9, wherein the breast fluid is additionally screened for the presence of at least one additional marker of breast cancer.

14. The method of claim 5, wherein the additional marker of breast cancer is an aldehyde marker comprising low molecular weight aldehydes that are soluble in water.

* * * * *